US012669115B2

(12) United States Patent
Payne et al.

(10) Patent No.: US 12,669,115 B2
(45) Date of Patent: *Jun. 30, 2026

(54) FLUID HANDLING ASSEMBLY AND RELATED TUBE SET AND METHOD FOR USE IN SURGICAL PROCEDURES

(71) Applicant: MISONIX, LLC, Farmingdale, NY (US)

(72) Inventors: Timothy John Payne, Santa Ana, CA (US); Scott Lavoy Conway, Yorba Linda, CA (US); Robert Paul Mayercheck, Irvine, CA (US)

(73) Assignee: Misonix, LLC, Farmingdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/389,084

(22) Filed: Nov. 13, 2023

(65) Prior Publication Data

US 2024/0410355 A1     Dec. 12, 2024

Related U.S. Application Data

(63) Continuation of application No. 17/235,308, filed on Apr. 20, 2021, now Pat. No. 11,821,417, which is a
(Continued)

(51) Int. Cl.
*A61M 1/00*         (2006.01)
*A61B 1/12*         (2006.01)
(Continued)

(52) U.S. Cl.
CPC ........... *F04B 43/1292* (2013.01); *A61M 1/77* (2021.05); *A61M 1/80* (2021.05); *A61M 3/0258* (2013.01);
(Continued)

(58) Field of Classification Search
CPC ............. A61M 5/14232; A61M 5/1408; F04B 43/1292
See application file for complete search history.

(56) References Cited

U.S. PATENT DOCUMENTS 4,155,362 A     5/1979   Jess
4,184,510 A     1/1980   Murry et al.
(Continued)

FOREIGN PATENT DOCUMENTS

CN        200953355 Y     9/2007
CN        101557843 A     10/2009
(Continued)

OTHER PUBLICATIONS

CA Application No. 3117126, Office Action mailed Mar. 11, 2025; Applicant Misonix, Inc.; 6 pages.
(Continued)

*Primary Examiner* — Laura A Bouchelle

(57)     ABSTRACT

A fluid handling system for a surgical procedure includes a console and a tubing set. The console exhibits a peristaltic pump, a pinch valve, one above the other. Two recessed seats are located to the left and right sides of the pump and valve. The tubing set includes an irrigation tube and an aspiration tube each coupled to a pair of magnetic disks disposable in respective ones of the recessed seats. Upon such disposition, the irrigation tube is disposable in operative engagement with the peristaltic pump and the aspiration tube is insertable into a slot of the pinch valve.

20 Claims, 3 Drawing Sheets

Related U.S. Application Data continuation of application No. 16/169,569, filed on Oct. 24, 2018, now Pat. No. 11,007,308.

(51) Int. Cl.

| | |
|---|---|
| *A61M 3/02* | (2006.01) |
| *F04B 43/12* | (2006.01) |
| *A61B 18/00* | (2006.01) |

(52) U.S. Cl.
CPC ..... *A61B 1/125* (2013.01); *A61B 2018/00011* (2013.01); *A61M 2205/3331* (2013.01)

(56) References Cited

U.S. PATENT DOCUMENTS

| | | | |
|---|---|---|---|
| 4,428,748 A | 1/1984 | Peyman et al. | |
| 4,604,089 A | 8/1986 | Santangelo et al. | |
| 4,764,165 A | 8/1988 | Reimels et al. | |
| 4,900,302 A | 2/1990 | Newton | |
| 4,921,477 A | 5/1990 | Davis | |
| 4,925,376 A | 5/1990 | Kahler | |
| 4,998,527 A | 3/1991 | Meyer | |
| 5,027,792 A | 7/1991 | Meyer | |
| 5,041,096 A | 8/1991 | Beuchat et al. | |
| 5,085,658 A | 2/1992 | Meyer | |
| 5,125,891 A | 6/1992 | Hossain et al. | |
| 5,190,448 A | 3/1993 | Lane et al. | |
| 5,213,483 A | 5/1993 | Flaherty et al. | |
| 5,242,404 A | 9/1993 | Conley et al. | |
| 5,267,956 A | 12/1993 | Beuchat | |
| 5,324,180 A | 6/1994 | Zanger | |
| 5,328,456 A | 7/1994 | Horiguchi et al. | |
| 5,360,398 A | 11/1994 | Grieshaber et al. | |
| 5,364,342 A | 11/1994 | Beuchat et al. | |
| 5,403,277 A | 4/1995 | Dodge et al. | |
| 5,429,601 A | 7/1995 | Conley et al. | |
| 5,433,588 A | 7/1995 | Monk et al. | |
| 5,460,490 A | 10/1995 | Carr et al. | |
| 5,465,468 A | 11/1995 | Manna | |
| 5,499,969 A | 3/1996 | Beuchat et al. | |
| 5,527,273 A | 6/1996 | Manna et al. | |
| 5,533,976 A | 7/1996 | Zaleski et al. | |
| 5,569,188 A | 10/1996 | Mackool | |
| 5,605,545 A | 2/1997 | Nowosielski et al. | |
| 5,630,798 A | 5/1997 | Beiser et al. | |
| 5,697,898 A | 12/1997 | Devine | |
| 5,697,910 A | 12/1997 | Cole et al. | |
| 5,700,240 A | 12/1997 | Barwick, Jr. et al. | |
| 5,733,256 A | 3/1998 | Costin | |
| 5,769,211 A | 6/1998 | Manna et al. | |
| 5,800,383 A | 9/1998 | Chandler et al. | |
| 5,810,770 A | 9/1998 | Chin et al. | |
| 5,810,776 A | 9/1998 | Bacich et al. | |
| 5,882,339 A | 3/1999 | Beiser et al. | |
| 5,897,524 A | 4/1999 | Wortrich et al. | |
| 5,910,110 A | 6/1999 | Bastable | |
| 5,927,956 A | 7/1999 | Lim et al. | |
| 6,033,375 A | 3/2000 | Brumbach | |
| 6,036,667 A | 3/2000 | Manna et al. | |
| 6,059,765 A | 5/2000 | Cole et al. | |
| 6,080,170 A | 6/2000 | Nash et al. | |
| 6,155,975 A | 12/2000 | Urich et al. | |
| 6,164,921 A | 12/2000 | Moubayed et al. | |
| 6,193,683 B1 | 2/2001 | Ludin et al. | |
| 6,261,283 B1 | 7/2001 | Morgan et al. | |
| 6,270,471 B1 | 8/2001 | Hechel et al. | |
| 6,283,974 B1 | 9/2001 | Alexander | |
| 6,290,690 B1 | 9/2001 | Huculak et al. | |
| 6,319,220 B1 | 11/2001 | Bylsma | |
| 6,319,223 B1 | 11/2001 | Wortrich et al. | |
| 6,375,648 B1 | 4/2002 | Edelman et al. | |
| 6,379,371 B1 | 4/2002 | Novak et al. | |
| 6,394,974 B1 | 5/2002 | Kadziauskas et al. | |
| 6,428,508 B1 | 8/2002 | Ross | |
| 6,440,103 B1 | 8/2002 | Hood et al. | |
| 6,443,969 B1 | 9/2002 | Novak et al. | |
| 6,454,730 B1 | 9/2002 | Hechel et al. | |
| 6,461,314 B1 | 10/2002 | Pant et al. | |
| 6,468,059 B2 | 10/2002 | Haser et al. | |
| 6,492,762 B1 | 12/2002 | Pant et al. | |
| 6,524,323 B1 | 2/2003 | Nash et al. | |
| 6,561,999 B1 | 5/2003 | Nazarifar et al. | |
| 6,569,147 B1 | 5/2003 | Evans et al. | |
| 6,575,969 B1 | 6/2003 | Rittman, III et al. | |
| 6,582,440 B1 | 6/2003 | Brumbach | |
| 6,613,056 B1 | 9/2003 | Brumbach et al. | |
| 6,629,948 B2 | 10/2003 | Rockley et al. | |
| 6,632,214 B2 | 10/2003 | Morgan et al. | |
| 6,648,839 B2 | 11/2003 | Manna et al. | |
| 6,652,546 B1 | 11/2003 | Nash et al. | |
| 6,723,065 B2 | 4/2004 | Kishimoto | |
| 6,736,814 B2 | 5/2004 | Manna et al. | |
| 6,740,074 B2 | 5/2004 | Morgan et al. | |
| 6,780,165 B2 | 8/2004 | Kadziauskas et al. | |
| 6,787,974 B2 | 9/2004 | Fjield et al. | |
| 6,799,729 B1 | 10/2004 | Voic | |
| 6,824,525 B2 | 11/2004 | Nazarifar et al. | |
| 6,830,577 B2 | 12/2004 | Nash et al. | |
| 6,843,797 B2 | 1/2005 | Nash et al. | |
| 6,869,439 B2 | 3/2005 | White et al. | |
| 6,902,536 B2 | 6/2005 | Manna et al. | |
| 6,905,505 B2 | 6/2005 | Nash et al. | |
| 6,908,451 B2 | 6/2005 | Brody et al. | |
| 6,936,056 B2 | 8/2005 | Nash et al. | |
| D513,801 S | 1/2006 | Stubkjaer | |
| 7,018,182 B2 * | 3/2006 | O'Mahony | F04B 43/1253 417/477.2 |
| 7,077,820 B1 | 7/2006 | Kadziauskas et al. | |
| 7,169,123 B2 | 1/2007 | Kadziauskas et al. | |
| 7,223,267 B2 | 5/2007 | Isola et al. | |
| 7,238,010 B2 | 7/2007 | Hershberger et al. | |
| 7,244,240 B2 | 7/2007 | Nazarifar et al. | |
| 7,273,359 B2 | 9/2007 | Blight et al. | |
| 7,316,664 B2 | 1/2008 | Kadziauskas et al. | |
| 7,367,982 B2 | 5/2008 | Nash et al. | |
| 7,392,144 B2 | 6/2008 | Sorensen et al. | |
| 7,442,168 B2 | 10/2008 | Novak et al. | |
| 7,469,727 B2 | 12/2008 | Marshall | |
| 7,485,106 B2 | 2/2009 | Kadziauskas et al. | |
| 7,534,249 B2 | 5/2009 | Nash et al. | |
| 7,556,481 B2 | 7/2009 | Moubayed | |
| 7,597,662 B2 | 10/2009 | Litscher et al. | |
| 7,611,500 B1 | 11/2009 | Lina et al. | |
| 7,625,388 B2 | 12/2009 | Boukhny et al. | |
| 7,632,079 B2 | 12/2009 | Hershberger et al. | |
| 7,644,603 B2 | 1/2010 | Gordon et al. | |
| 7,645,255 B2 | 1/2010 | Gordon et al. | |
| 7,713,202 B2 | 5/2010 | Boukhny et al. | |
| 7,717,913 B2 | 5/2010 | Novak et al. | |
| 7,722,582 B2 | 5/2010 | Lina et al. | |
| 7,727,179 B2 | 6/2010 | Barrett | |
| 7,727,193 B2 | 6/2010 | Boukhny et al. | |
| 7,753,880 B2 | 7/2010 | Malackowski | |
| 7,758,538 B2 | 7/2010 | Boukhny et al. | |
| 7,776,027 B2 | 8/2010 | Manna et al. | |
| 7,785,316 B2 | 8/2010 | Claus et al. | |
| 7,785,336 B2 | 8/2010 | Staggs | |
| 7,811,255 B2 | 10/2010 | Boukhny et al. | |
| 7,824,384 B2 | 11/2010 | Watson, Jr. | |
| 7,842,005 B2 | 11/2010 | Kadziauskas et al. | |
| 7,846,126 B2 | 12/2010 | Steen et al. | |
| 7,857,783 B2 | 12/2010 | Kadziauskas et al. | |
| 7,883,489 B2 | 2/2011 | Guignard | |
| 7,931,611 B2 | 4/2011 | Novak et al. | |
| 7,938,120 B2 | 5/2011 | Kadziauskas et al. | |
| 7,942,853 B2 | 5/2011 | Svetic | |
| 7,947,009 B2 | 5/2011 | Kübler et al. | |
| 7,964,766 B2 | 6/2011 | Blott et al. | |
| 7,981,129 B2 | 7/2011 | Nash et al. | |
| 7,998,156 B2 | 8/2011 | Staggs | |
| 8,020,565 B2 | 9/2011 | Kadziauskas et al. | |
| 8,025,672 B2 | 9/2011 | Novak et al. | |
| RE42,834 E | 10/2011 | Watson | |
| 8,034,067 B2 | 10/2011 | Staggs | |

(56)                    References Cited

U.S. PATENT DOCUMENTS

| | | | |
|---|---|---|---|
| 8,048,020 B2 | 11/2011 | Boukhny et al. |
| 8,070,712 B2 | 12/2011 | Muri et al. |
| 8,080,702 B2 | 12/2011 | Blott et al. |
| 8,083,671 B2 | 12/2011 | Boulais et al. |
| 8,092,427 B2 | 1/2012 | Urich et al. |
| 8,109,925 B2 | 2/2012 | Voic et al. |
| 8,118,794 B2 | 2/2012 | Weston |
| 8,128,384 B2 | 3/2012 | Mou |
| 8,162,909 B2 | 4/2012 | Blott et al. |
| 8,177,776 B2 | 5/2012 | Humayun et al. |
| 8,195,286 B2 | 6/2012 | Kadziauskas et al. |
| 8,197,436 B2 | 6/2012 | Kadziauskas et al. |
| 8,202,243 B2 | 6/2012 | Morgan |
| 8,202,262 B2 | 6/2012 | Lina et al. |
| 8,202,287 B2 | 6/2012 | Staggs |
| 8,221,402 B2 | 7/2012 | Francischelli et al. |
| 8,226,673 B2 | 7/2012 | Nash et al. |
| 8,231,564 B2 | 7/2012 | Kadziauskas et al. |
| 8,257,307 B2 | 9/2012 | Boukhny et al. |
| 8,272,857 B2 | 9/2012 | Norman et al. |
| 8,303,530 B2 | 11/2012 | Injev et al. |
| 8,308,703 B2 | 11/2012 | Heaton et al. |
| 8,343,178 B2 | 1/2013 | Novak et al. |
| 8,353,912 B2 | 1/2013 | Darian et al. |
| 8,366,728 B2 | 2/2013 | Staggs |
| 8,398,582 B2 | 3/2013 | Gordon et al. |
| 8,403,851 B2 | 3/2013 | Boukhny et al. |
| 8,414,534 B2 | 4/2013 | Bandhauer et al. |
| 8,425,452 B2 | 4/2013 | Claus et al. |
| 8,430,838 B2 | 4/2013 | Gordon et al. |
| 8,430,897 B2 | 4/2013 | Novak et al. |
| 8,449,509 B2 | 5/2013 | Weston |
| 8,460,255 B2 | 6/2013 | Joshi et al. |
| 8,491,528 B2 | 7/2013 | Muri et al. |
| 8,523,812 B2 | 9/2013 | Boukhny et al. |
| 8,535,296 B2 | 9/2013 | Blott et al. |
| 8,579,929 B2 | 11/2013 | Mackool et al. |
| 8,603,123 B2 | 12/2013 | Todd |
| 8,617,106 B2 | 12/2013 | Zacharias |
| 8,623,000 B2 | 1/2014 | Humayun et al. |
| 8,628,505 B2 | 1/2014 | Weston |
| 8,652,102 B2 | 2/2014 | Nitsan et al. |
| 8,659,208 B1 | 2/2014 | Rose et al. |
| 8,679,062 B2 | 3/2014 | Yodfat et al. |
| 8,690,783 B2 | 4/2014 | Sinelnikov |
| 8,698,377 B2 | 4/2014 | Sinelnikov |
| 8,721,594 B2 | 5/2014 | Zacharias |
| 8,758,313 B2 | 6/2014 | Blott et al. |
| 8,801,653 B2 | 8/2014 | Maaskamp et al. |
| 8,814,821 B2 | 8/2014 | Steen et al. |
| 8,814,870 B2 | 8/2014 | Paraschiv et al. |
| 8,834,451 B2 | 9/2014 | Blott et al. |
| 8,852,138 B2 | 10/2014 | Kadzlauskas et al. |
| 8,876,747 B2 | 11/2014 | Kadziauskas et al. |
| 8,882,662 B2 | 11/2014 | Charles |
| 8,887,735 B2 | 11/2014 | Kadzlauskas et al. |
| 8,894,673 B2 | 11/2014 | Darian |
| 8,926,592 B2 | 1/2015 | Blott et al. |
| 8,939,927 B2 | 1/2015 | Sorensen et al. |
| 8,945,162 B2 | 2/2015 | Kadziauskas et al. |
| 8,974,412 B2 | 3/2015 | Boukhny et al. |
| 9,039,719 B2 | 5/2015 | Todd |
| 9,044,569 B2 | 6/2015 | Blott et al. |
| 9,070,856 B1 | 6/2015 | Rose et al. |
| 9,072,540 B2 * | 7/2015 | Jarnagin ................ A61M 1/80 |
| 9,078,964 B2 | 7/2015 | Schuman, Jr. |
| 9,200,628 B2 | 12/2015 | Zupp et al. |
| 9,205,001 B2 | 12/2015 | Blott et al. |
| 9,205,186 B2 | 12/2015 | Tarkeshian et al. |
| 9,211,137 B2 | 12/2015 | Voic |
| 9,216,068 B2 | 12/2015 | Tesar |
| 9,226,849 B2 | 1/2016 | Staggs |
| 9,227,088 B2 | 1/2016 | Hissong et al. |
| 9,272,080 B2 | 3/2016 | Weston |
| 9,282,989 B2 | 3/2016 | Boukhny et al. |
| 9,289,110 B2 | 3/2016 | Woolford et al. |
| 9,295,582 B2 | 3/2016 | Rockley et al. |
| 9,295,765 B2 | 3/2016 | Muri et al. |
| 9,314,553 B2 | 4/2016 | Gordon et al. |
| 9,320,528 B2 | 4/2016 | Voic et al. |
| 9,386,922 B2 | 7/2016 | Ross et al. |
| 9,387,005 B2 | 7/2016 | Voic |
| 9,393,070 B2 | 7/2016 | Gelfand et al. |
| 9,393,152 B2 | 7/2016 | Wong et al. |
| 9,433,723 B2 | 9/2016 | Steen et al. |
| 9,445,943 B2 | 9/2016 | Wilson et al. |
| 9,452,248 B2 | 9/2016 | Blott et al. |
| 9,492,065 B2 | 11/2016 | Tesar et al. |
| 9,492,071 B2 | 11/2016 | Woolford et al. |
| 9,492,317 B2 | 11/2016 | Links |
| 9,510,853 B2 | 12/2016 | Aljuri et al. |
| 9,511,184 B2 | 12/2016 | Woolford et al. |
| 9,522,221 B2 | 12/2016 | Muri et al. |
| 9,545,334 B2 | 1/2017 | Steen et al. |
| 9,545,336 B2 | 1/2017 | Sussman |
| 9,549,751 B2 | 1/2017 | Todd |
| 9,549,849 B2 | 1/2017 | Charles |
| 9,561,321 B2 | 2/2017 | Sorensen et al. |
| 9,566,188 B2 | 2/2017 | Raney et al. |
| 9,603,990 B2 | 3/2017 | Woolford |
| 9,615,728 B2 | 4/2017 | Charles et al. |
| 9,622,766 B2 | 4/2017 | Voic |
| 9,629,523 B2 | 4/2017 | Tesar et al. |
| 9,636,187 B2 | 5/2017 | Voic |
| 9,642,606 B2 | 5/2017 | Charles et al. |
| 9,642,745 B2 | 5/2017 | Kadziauskas et al. |
| 9,675,373 B2 | 6/2017 | Todd |
| 9,681,796 B2 | 6/2017 | Tesar et al. |
| 9,693,792 B2 | 7/2017 | Novak et al. |
| 9,693,896 B2 | 7/2017 | Sussman |
| 9,700,457 B2 | 7/2017 | Gerg et al. |
| 9,702,355 B2 | 7/2017 | Bourne et al. |
| 9,707,127 B2 | 7/2017 | Kadziauskas et al. |
| 9,723,976 B2 | 8/2017 | Tesar |
| 9,724,119 B2 | 8/2017 | Hissong et al. |
| 9,730,833 B2 | 8/2017 | Humayun et al. |
| 9,750,638 B2 | 9/2017 | Bourne et al. |
| 9,757,180 B2 | 9/2017 | Gelfand et al. |
| 9,757,275 B2 | 9/2017 | Muri et al. |
| 9,782,159 B2 | 10/2017 | Tesar |
| 9,788,998 B2 | 10/2017 | Kadziauskas et al. |
| 9,795,507 B2 | 10/2017 | Hajishah et al. |
| 9,844,473 B2 | 12/2017 | Blott et al. |
| 9,848,904 B2 | 12/2017 | Aljuri et al. |
| 9,872,697 B2 | 1/2018 | Voic |
| 9,877,865 B2 | 1/2018 | Links |
| 9,878,075 B2 | 1/2018 | Sussman et al. |
| 9,889,246 B2 | 2/2018 | Woolford |
| 9,895,262 B2 | 2/2018 | Ross et al. |
| 9,931,134 B2 | 4/2018 | Hissong et al. |
| 9,936,863 B2 | 4/2018 | Tesar |
| 9,949,751 B2 | 4/2018 | Voic |
| 9,962,472 B2 | 5/2018 | Woolford et al. |
| 9,968,371 B2 | 5/2018 | Todd |
| 10,022,041 B2 | 7/2018 | Charles et al. |
| 10,052,227 B2 | 8/2018 | Saimovici |
| 10,076,349 B2 | 9/2018 | Voic |
| 10,076,442 B2 | 9/2018 | Wong et al. |
| 10,092,308 B2 | 10/2018 | Mikus et al. |
| 10,092,741 B2 | 10/2018 | Darian |
| 10,117,666 B2 | 11/2018 | Voic |
| 10,182,837 B2 | 1/2019 | Isola et al. |
| 10,206,704 B2 | 2/2019 | Voic et al. |
| 10,299,809 B2 | 5/2019 | Mikus et al. |
| 10,398,463 B2 | 9/2019 | Darian et al. |
| 10,398,465 B2 | 9/2019 | Darian |
| 10,405,875 B2 | 9/2019 | Voic et al. |
| 10,463,381 B2 | 11/2019 | Voic et al. |
| 10,470,788 B2 | 11/2019 | Sinelnikov |
| 10,470,789 B2 | 11/2019 | Mikus et al. |
| 10,471,281 B2 | 11/2019 | Mikus |
| 10,543,012 B2 | 1/2020 | Pantano |
| 10,835,276 B2 | 11/2020 | Voic et al. |
| 10,842,587 B2 | 11/2020 | Mikus et al. |

(56)    References Cited

U.S. PATENT DOCUMENTS

| 11,007,308 B2 | 5/2021 | Payne et al. |
| 11,298,434 B2 | 4/2022 | Isola et al. |
| 11,324,531 B2 | 5/2022 | Voic et al. |
| 11,672,558 B2 | 6/2023 | Voic |
| 11,737,775 B2 | 8/2023 | Voic et al. |
| 11,821,417 B2 * | 11/2023 | Payne ................. A61M 3/0258 |
| 11,950,790 B2 | 4/2024 | Voic |
| 12,011,190 B2 | 6/2024 | Theodore et al. |
| 2008/0154095 A1 | 6/2008 | Stubkjaer et al. |
| 2009/0043252 A1 | 2/2009 | Haylor et al. |
| 2009/0285706 A1 | 11/2009 | Bunoz |
| 2011/0300010 A1 | 12/2011 | Jarnagin et al. |
| 2012/0065482 A1 | 3/2012 | Robinson et al. |
| 2013/0131585 A1 | 5/2013 | Eubanks et al. |
| 2013/0226042 A1 | 8/2013 | Novak et al. |
| 2013/0231528 A1 | 9/2013 | Voic |
| 2014/0180002 A1 | 6/2014 | Voic |
| 2014/0277034 A1 | 9/2014 | Darian |
| 2015/0088137 A1 | 3/2015 | Manna |
| 2015/0094723 A1 | 4/2015 | Darian |
| 2016/0287779 A1 | 10/2016 | Orczy-Timko et al. |
| 2021/0267622 A1 | 9/2021 | Ellegala |
| 2023/0048993 A1 | 2/2023 | Levy et al. |
| 2023/0210549 A1 | 7/2023 | Voic et al. |

FOREIGN PATENT DOCUMENTS

| CN | 102711866 A | 10/2012 |
| CN | 203825244 U | 9/2014 |
| CN | 106801777 A | 6/2017 |
| JP | 2013192712 A | 9/2013 |
| WO | WO-2017083733 A1 | 5/2017 |

OTHER PUBLICATIONS

CN Application No. 201880098951.3, Office Action mailed Dec. 28, 2024; Applicant Misonix, Inc.; 30 pages with English translation.

CN Application No. 201880098951.3, Office Action mailed Jul. 23, 2024; Applicant Misonix, Inc.; 20 pages with English translation.

EP Application No. 18938154.4, Extended European Search Report mailed May 10, 2022; Applicant Misonix, Inc.; 15 pages.

EP Application No. 18938154.4, Office Action mailed Dec. 11, 2024; Applicant Misonix, Inc.; 7 pages.

JP Application No. 2021-522362, Office Action mailed May 29, 2023; Applicant Misonix, Inc.; 4 pages with English translation.

JP Application No. 2021-522362, Office Action mailed Nov. 4, 2022; Applicant Misonix, Inc.; 26 pages with English translation.

PCT Application No. PCT/US2018/057070, International Preliminary Report on Patentability mailed May 6, 2021; Applicant Misonix, Inc.; 6 pages.

PCT Application No. PCT/US2018/057070, International Search Report and Written Opinion mailed Jul. 18, 2019; Applicant Misonix, Inc; 6 pages.

U.S. Appl. No. 16/169,569, Final Office Action mailed Oct. 20, 2020; inventor Payne, Timothy John et al.; 8 pages.

U.S. Appl. No. 16/169,569, Non-Final Office Action mailed May 27, 2020; inventor Payne, Timothy John et al.; 18 pages.

U.S. Appl. No. 17/235,308, Non-Final Office Action mailed May 3, 2023; inventor Payne, Timothy John et al.; 11 pages.

* cited by examiner

FLUID HANDLING ASSEMBLY AND RELATED TUBE SET AND METHOD FOR USE IN SURGICAL PROCEDURES

CROSS-REFERENCE TO RELATED APPLICATION

This application is a continuation of application Ser. No. 17/235,308 filed Apr. 20, 2021, which is a continuation of application Ser. No. 16/169,569 filed Oct. 24, 2018 now U.S. Pat. No. 11,007,308.

BACKGROUND OF THE INVENTION

The present invention relates to moving fluids in surgical procedures. More particularly, this invention relates to a fluid handling assembly including a console and a disposable tubing set. This invention also relates to the tubing set for use with the console. The invention also pertains to a method including the disposition of tubing in association with a pump and a pinch valve. The method is of particular use in ultrasonic surgical procedures, for irrigating and removing debris from a surgical site.

In ultrasonic surgical procedures, the head of an ultrasonically vibrating probe is placed into pressure-wave transmitting contact with tissue of a patient. The probe may be an ablating device, a debriding instrument, or a suction instrument, among others. Using an ultrasonic probe requires the delivery of an irrigant to the instrument and to the tissue in order to prevent temperature elevation to a degree that would cause necrosis. The cooling liquid must naturally be removed from the site into order to make way for further coolant. The removal entails suction that also removes entrained tissue particles.

Surgical equipment includes irrigation tubing and suction tubing as well as a pump mechanism for moving the irrigant to the surgical site, for instance, via the ultrasonic probe or a sheath surrounding the probe, and an aspiration or vacuum source connected to the suction tubing. A technician generally sets up the fluid handling circuits prior to the surgical procedure. On occasion, there are errors such as mixing the irrigation tubing and the suction tubing, which prevents proper operation of the assembly.

SUMMARY OF THE INVENTION

The present invention aims to provide a tubing set and associated console that facilitate the preparation of a fluids handling system prior to surgery.

The present invention further aims to provide such a tubing set and associated console that significantly reduce, if not eliminate, errors in setting up a surgical fluids handling assembly.

The present invention also contemplates an associated method of setting up a fluids handling assembly or system.

A fluid handling system for a surgical treatment comprises, in accordance with the present invention, a console and a tubing set.

The console includes a housing having a panel, a peristaltic pump, a pinch valve, and a first seat and a second seat on the housing panel. The peristaltic pump is mounted to the housing and extends outwardly from the panel. More specifically, the pump includes a roller set and an anvil that are movably attached to a pump casing, the roller set being rotatable about an axis perpendicular to the housing panel and the anvil being movable from a neutral position to a closed position for clamping a tube between the roller set and a curved inside surface of the anvil. The pinch valve is mounted to the housing panel and has a slot or gap between two jaws movable relative to one another to selectively restrict flow through a tube inserted into the slot. The peristaltic pump and the pinch valve are spaced from one another along a line. The seats are disposed on the housing panel on opposite sides of the line.

The tubing set, which is intended to be disposable rather than reusable, includes an irrigation tube, an aspiration tube, a first attachment element, and a second attachment element. The irrigation tube and the aspiration tube are each coupled to both the first attachment element and the second attachment element. The first attachment element is seatable in the first seat on the console housing panel while the second attachment element is seatable in the second seat. The irrigation tube and the aspiration tube are coupled to the first attachment element and the second attachment element so that the irrigation tube and the aspiration tube extend in spaced relation to one another between the first attachment element and the second attachment element, at least when the attachment elements are spaced from one another by a distance approximately equal to the distance between the first seat and the second seat on the console panel. The irrigation tube is positionable in operative engagement with the roller set and the anvil while the aspiration tube is insertable into the slot of the pinch valve upon seating of the first attachment element in the first seat and seating of the second attachment element in the second seat.

The console preferably further comprises first coupling elements at the first seat and the second seat, while the first attachment element and the second attachment element include second coupling elements that cooperate with respective ones of the first coupling elements to releasably fasten the first attachment element and the second attachment element to the housing panel at the first seat and the second seat, respectively.

The coupling elements may include magnets. Other, alternative, coupling elements may take the form of snap-lock fasteners, adhesive layers, hook-and-loop fasteners, etc.

Pursuant to another feature of the present invention, the seats are recesses of different geometries in the console housing panel. The first attachment element and the second attachment element have geometries corresponding to the geometries of respective ones of the recesses. Thus at least one of the attachment elements, said the second element, is disposable only in the second seat and cannot be seated in the first seat owing to a mismatch in size or shape.

Pursuant to additional features of the present invention, the first attachment element and the second attachment element are disks of different sizes, the first seat and the second seat having different sizes congruent with respective ones of the disks. The disks may be provided on one side (an outer side) with finger grips for facilitate manipulation of the tubing set during assembly of the fluid handling system.

The console may further include a plurality of indicators such as LED lights that signal successful seating of the first attachment element and the second attachment element in the first seat and the second seat, respectively, and successful placement of the irrigation tube between the roller set and the anvil of the peristaltic pump.

The console may also include an air bubble detector at the second seat. The air bubble detector is so located to be juxtaposed to the irrigation tube upon seating of the second attachment element in the second seat. More particularly, the air bubble detector may be housed in a projection on the second seat that is inserted into a hole in the rear or inner side of the second attachment element. The irrigation tube extends across the hole so as to automatically insert into a slot in the projection upon the seating of the second attachment element in the second seat on the housing panel of the console. The air bubble detector may take the form of an ultrasound sensor.

The panel is preferably a side panel of the housing, and the peristaltic pump and the pinch valve are preferably located vertically one above the other.

The present invention is directed in part to a fluid handling tubing set for use in surgical interventions. The tubing set, described above, is utilizable with a console as described above.

Concomitantly, the present invention contemplates a console as described above.

A surgical method in accordance with the present invention comprises providing a tubing set for carrying fluids, the tubing set including a first tube, a second tube, a first attachment element, and a second attachment element, the first tube and the second tube each being coupled to both the first attachment element and the second attachment element. The first attachment element and the second attachment element have different geometries. The method includes seating the first attachment element in a first seat on a panel of a console and seating the second attachment element in a second seat on the panel of the console so that the first tube and the second tube extend in spaced relation to one another between the first attachment element and the second attachment element. Thereafter, the first tube is manipulated so as to dispose a portion of the first tube in operative engagement with a roller set and an anvil of the console projecting from the panel, and the second tube is manipulated so as to insert the second tube into a slot or gap of a pinch valve of the console projecting from the panel.

DETAILED DESCRIPTION

A fluid handling system 10 for use in a surgical treatment procedure includes a console 12 and a tubing set 14.

Figure 1:
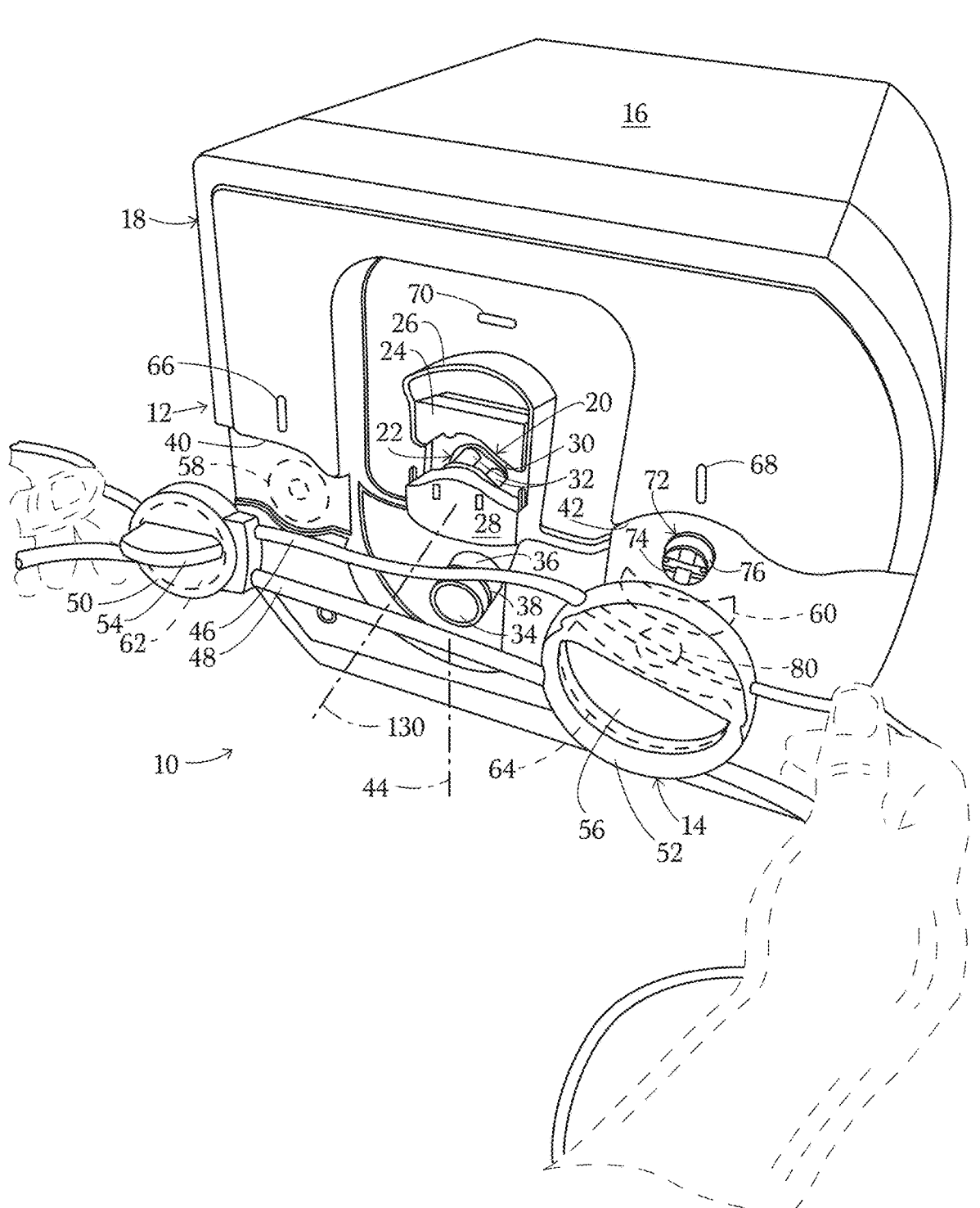
FIG. 1 is a perspective view of a fluid handling system particularly including a tubing set and a console, showing the tubing set spaced from an d in position for attachment to the console, in accordance with the present invention.

Console 12 includes a housing 16 with a side panel 18. A peristaltic pump 20 is mounted to housing 16 on side panel 18 and includes a roller set 22 and an anvil 24, as well as a cover 26. Roller set 22 is held at an outer end by a bracket 28 for rotation about an axis 30 oriented perpendicular to panel 18. Cover 26 is hingedly mounted to a pump casing (not separately designated) and, when rotated downwardly from a neutral position shown in FIG. 1 to a closed position shown in FIG. 3, moves anvil 24 toward roller set 22, so that a curved surface or face 30 of the anvil is placed adjacent to rollers 32 of roller set 22.

Console 12 further includes a solenoid-operated pinch valve 34 that comprises two relatively movable jaws (not separately designated) disposed inside a sleeve 36 mounted to panel 18 and formed with a transverse slot 38. Pinch valve 34 is spaced from peristaltic pump 20, including roller set 22 and anvil 24, in a plane or direction parallel to panel 18.

Console 12 further includes, molded into side panel 18, a first seat 40 and a second seat 42 in the form of circular or oval recesses of different geometries. More specifically, seats 40 and 42 may be of different shapes and/or different sizes. In the embodiment illustrated in the drawings, seat 42 is larger than seat 40.

Peristaltic pump 20 and solenoid pinch valve 34 are disposed one above the other and thereby define a vertical line or plane 44. Seats 40 and 42 are disposed on side panel 18 on opposite sides of line or plane 44.

Tubing set 14 includes an irrigation tube 46, an aspiration tube 48, a first attachment disk 50, and a second attachment disk 52. Irrigation tube 46 and aspiration tube 48 are each coupled to both first attachment disk 50 and second attachment disk 52. Disks 50 and 52 may be formed by bonding two half disks to one another, sandwiching tubes 46 and 48 between the half disks in each case. Disks 50 and 52 are each provided on major outer side or face (not designated) with a respective finger grip 54 and 56 in the form of a ring or flange projecting orthogonally to the respective major outer side or face for facilitating manipulation of the disks during an assembly procedure.

Typically, a technician grasping finger grips 54 and 56 will place disks 50 and 52 in recesses or seats 40 and 42 with major outer sides or faces of the disks in the seats so that the disks extend in parallel relation to each other and panel 18. Attachment is of a quick-release type owing to magnets 58 and 60 (or magnets and metal elements) positioned in housing 16 adjacent seats 40 and 42 and magnetic counterparts 62 and 64 attached to disks 50 and 52. Alternative coupling elements such as snap-lock fasteners, adhesive layers, hook-and-loop fasteners, etc., may be used instead of magnets.

Disks 50 and 52 have different geometries, that is, different sizes and/or shapes, that are respectively congruent with the geometries of seats 40 and 42 so that disks 50 and 52 are seatable only in seats 40 and 42, respectively. This ensures that irrigation tube 46 is located above aspiration tube 48 once attachment disks 50 and 52 are seated on panel 18. Irrigation tube 46 and aspiration tube 48 are coupled to attachment disks 50 and 52 so that tubes 46 and 48 extend in spaced relation to one another between the disks and in a plane parallel to panel 18, when the disks are placed into seats 40 and 42.

Figure 2:
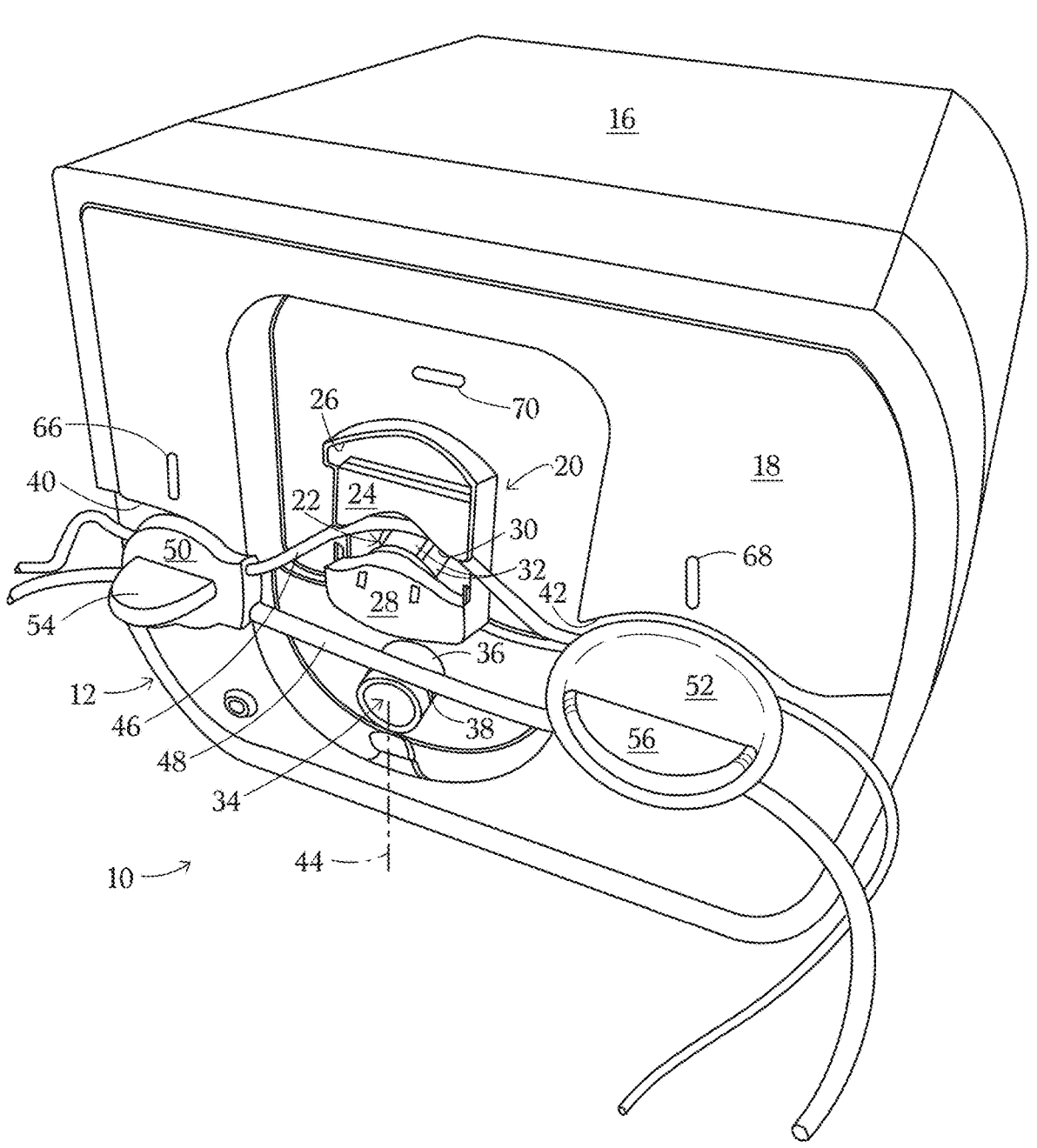
FIG. 2 is a perspective view of the system of FIG. 1, showing the tubing system positioned on the console, with an irrigation tube between an anvil and a roller set of a peristaltic pump.
Figure 3:
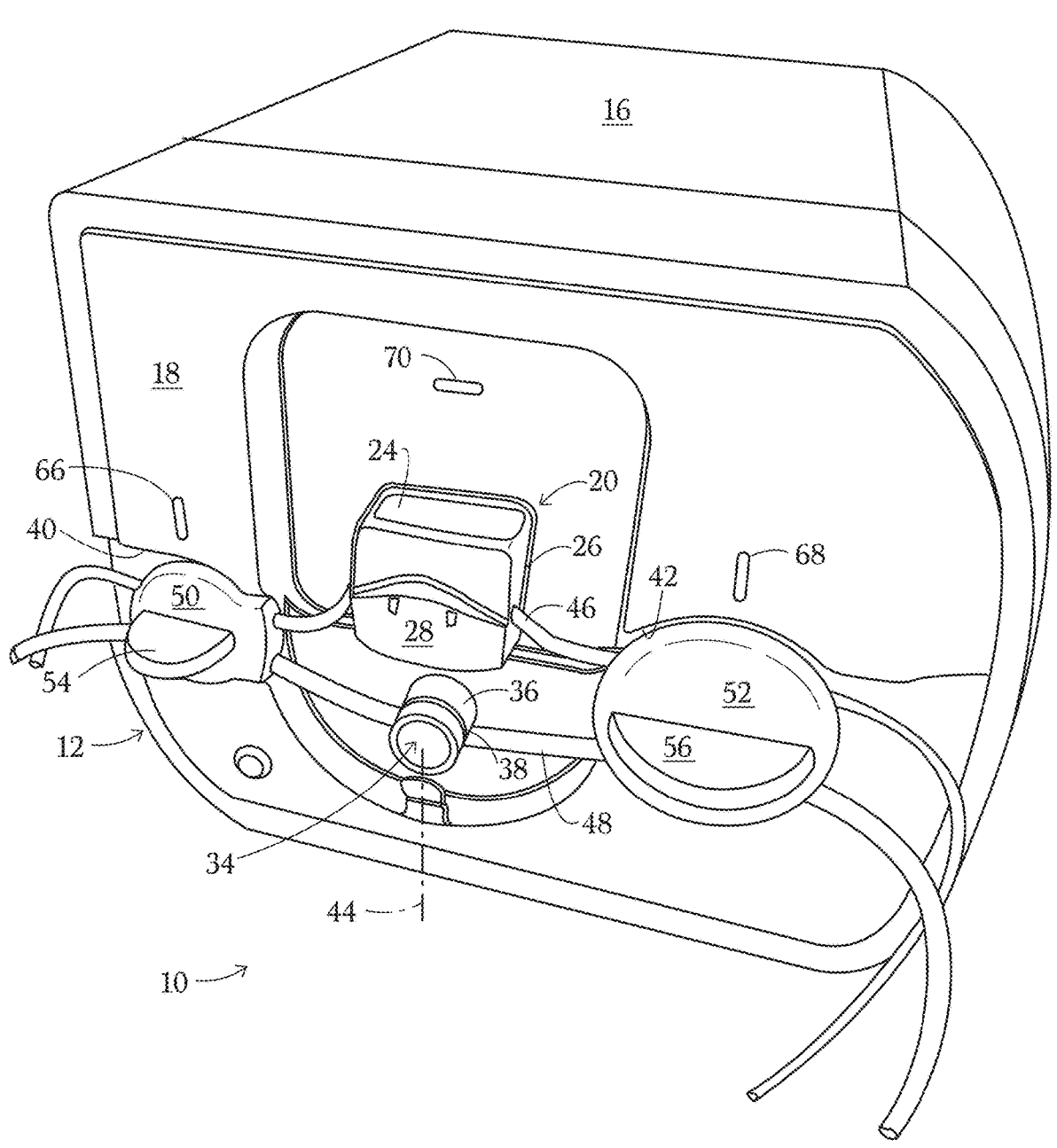
FIG. 3 is a perspective view similar to FIG. 2, showing a cover of the peristaltic pump closed over the irrigation tube and further showing an aspiration tube inserted between jaws (or an anvil and jaw) of a pinch solenoid on the console.

Disks 50 and 52 are spaced from one another by lengths of tubes 46 and 48 that are approximately equal (and slightly greater) to the distance between seats 40 and 42. Disks 50 and 52 are held and manipulated via flanges or finger grips 54 and 56, to engage housing side panel 18 in recesses or seats 40 and 42. Upon a disposition of disks 50 and 52 in seats 40 and 42, irrigation tube 46 is placed over roller set 22 in a gap between anvil 24 and bracket 28, as shown in FIG. 2. One then rotates the cover 26, which is pivotably mounted to housing 16 via anvil 24, thereby moving the anvil towards roller set 22 and clamping tube 46 between anvil surface 30 and the rollers 32, as illustrated in FIG. 3. As further shown in FIG. 3, aspiration tube 48 is inserted into slot 38 of pinch valve 34.

Console 12 exhibits indicators lights 66, 68, 70 that turn from one color, such as red or blue to another color such as green upon a successful seating of disks 50 and 52 in seats 40 and 42 and a successful or effective disposition of tube 46 between pump set 22 and surface 30 of anvil 24.

Console 12 may also include an air bubble detector 72 within seat 42. Bubble detector 72 preferably takes the form of an ultrasonic sensor with transmitter and receiver elements (not separately depicted) disposed in respective halves 74 and 76 of a slotted projection. During a seating of attachment or coupling disk 52 in recess or seat 42, the detector 72 is inserted into a hole 80 in the rear or inner side of attachment disk 52. Irrigation tube 46 extends across the hole 80 so as to automatically insert into a slot (not designated) defined between receiver halves 74 and 76 in the detector 72 upon the seating of attachment disk 52 in seat 42.

Panel 18 is preferably a side panel of housing 16, and peristaltic pump 20 and pinch valve 34 are preferably located vertically one above the other. However different configurations are possible. The essential feature is that the shapes and or sizes of disks 50 and 52, as well as seats 40 and 42, preclude an incorrect positioning of tubes 46 and 48. Upon the placements of disks 50 and 52 in recesses 40 and 42, it is not possible to position aspiration tube 48 on roller set 22 in the gap between anvil 24 and bracket or bearing plate 28. Only irrigation tube 46 is positionable there.

Prior to an ultrasonic surgical procedure, wherein liquid irrigant or coolant is furnished to an ultrasonic instrument via tube 46 and removed from the surgical site via tube 48, tubing set 14 is manipulated as described above so as to dispose a portion of tube 46 in operative engagement with roller set 22 and anvil 24, and a portion of tube 48 is inserted into slot or gap 38 of pinch valve 34.

Pursuant to the present invention, tubing set 14 includes irrigant tube 46 and suction or aspiration tube 48 connected in parallel to one another via a pair of spaced fasteners, that is, disks 50 and 52. Fasteners or attachment disks 50 and 52 include magnetic elements and have with planar projections 54 and 56 that serve as grips for grasping between the forefingers and thumbs by a technician. Disks 50 and 52 are juxtaposed to delineated positions (recesses or seats 40 and 42) on side panel 18 of console 16 where the disks are secured to the console in a quick-release mode of attachment, owing to magnetic attraction. Console panel 18 features well-known prior-art peristaltic pump 20 and a well-known pinch solenoid 34 that are spaced from one another. Disks 50 and 52 are attached to console 16 on opposite sides of an imaginary line 44 or plane extending defined by the locations of peristaltic pump 22 and pinch solenoid 34, preferably one located above the other. After the magnetic attachment, irrigation tube 46 is inserted over the rollers 32 of pump 20 and a cover- or lid-type anvil 24 is pivoted into place so that irrigation tube 46 is pressed between the pump rollers 32 and a curved inner surface 30 of the anvil. Aspiration tube 48 is placed in a gap 38 defined between jaws (not visible owing to sleeve 36) of pinch solenoid 34. Tubing set 14 simplifies the process of tube placement, making it impossible to insert the aspiration tube 48 into peristaltic pump 20.

Disk 50 or 52 may be provided with an RFID tag or chip (not shown) that may be set by a transmitter in housing 16 to prevent re-use of the tubing set 14, primarily for ensuring sterility.

Although the invention has been described in terms of particular embodiments and applications, one of ordinary skill in the art, in light of this teaching, can generate additional embodiments and modifications without departing from the spirit of or exceeding the scope of the claimed invention. Moreover, the phase shift might be varying, for instance, where the vibration modes are of different frequencies. Accordingly, it is to be understood that the drawings and descriptions herein are proffered by way of example to facilitate comprehension of the invention and should not be construed to limit the scope thereof.

What is claimed is:

1. An apparatus, comprising:
a housing having a panel;
a peristaltic pump mounted to the housing and extending outwardly from said panel;
a pinch valve mounted to the housing, the peristaltic pump and the pinch valve being spaced along a line from one another; and
a first seat and a second seat on the panel on opposite sides of the line, the first seat having a first geometric configuration and the second seat having a second geometric configuration different from the first geometric configuration, the first seat configured to receive a first attachment element and the second seat configured to receive a second attachment element such that such that an irrigation tube and an aspiration tube extending between the first and second attachment elements are positioned to engage with the peristaltic pump and the pinch valve, respectively.

2. The apparatus defined in claim 1, wherein the apparatus further includes:
coupling elements that cooperate with coupling elements on the first attachment element and the second attachment element to releasably fasten the first attachment element and the second attachment element to the panel at the first seat and the second seat, respectively.

3. The apparatus defined in claim 2, wherein at least a plurality of the coupling elements include magnets.

4. The apparatus defined in claim 2, wherein the first attachment element and the second attachment element are disks of different sizes.

5. The apparatus defined in claim 1, wherein the first attachment element and the second attachment element have different geometries.

6. A fluid handling system for a surgical treatment, comprising:
an irrigation tube;
an aspiration tube;
a first attachment element having a first geometry seatable in a first seat of a panel of a console; and
a second attachment element having a second geometry seatable in a second seat of the panel of the console, the second geometry being different from the first geometry,
the irrigation tube and the aspiration tube each being coupled to both the first attachment element and the second attachment element so that the irrigation tube and the aspiration tube extend between the first attachment element and the second attachment element upon seating of the first attachment element in the first seat and seating of the second attachment element in the second seat,
the irrigation tube being disposable in operative engagement with a peristaltic pump, and the aspiration tube being insertable into a pinch valve, upon seating of the first attachment element in the first seat and seating of the second attachment element in the second seat.

7. The fluid handling system defined in claim 6, wherein the console further comprises first coupling elements at the first seat and the second seat and wherein the first attachment element and the second attachment element include respective second coupling elements that cooperate with respective ones of the first coupling elements to releasably fasten the first attachment element and the second attachment element to the panel at the first seat and the second seat, respectively.

8. The fluid handling system defined in claim 7, wherein the first attachment element and the second attachment element are disks of different sizes, the first seat and the second seat having different sizes congruent with respective ones of the disks.

9. The fluid handling system defined in claim 8, wherein the first attachment element and the second attachment element are each provided on an outer side or face with a finger grip in the form of a ring or flange projecting orthogonally to the outer side or face.

10. The fluid handling system defined in claim 7, wherein the first coupling elements and the second coupling elements include magnets.

11. The fluid handling system defined in claim 6 wherein the console further includes a plurality of indicators that signal successful seating of the first attachment element and the second attachment element in the first seat and the second seat, respectively, and successful engagement of the irrigation tube to the peristaltic pump.

12. The fluid handling system defined in claim 11, wherein the plurality of indicators are lights.

13. The fluid handling system defined in claim 6, wherein the console further includes an air bubble detector at the second seat, the air bubble detector being located to be juxtaposed to the irrigation tube upon seating of the second attachment element in the second seat.

14. The fluid handling system defined in claim 13, wherein the air bubble detector is an ultrasound sensor.

15. The fluid handling system defined in claim 6, wherein the first seat and the second seat are recesses of different geometries in the panel.

16. The fluid handling system defined in claim 6, wherein the panel is a side panel of a housing, the peristaltic pump and the pinch valve being located vertically one above the other.

17. A tubing set for carrying fluids in a surgical procedure, comprising:

a first tube;

a second tube;

a first attachment element provided on a first side with a first geometric configuration and configured on a second side opposite the first side to enable manual manipulation of the first attachment element to seat the first attachment element in a first seat on a panel of a console; and a second attachment element provided on a respective first side with second geometric configuration and configured on a respective second side opposite the respective first side to enable manual manipulation of the second attachment element to seat the second attachment element in a second seat on the panel of the console, the first tube and the second tube each being coupled to both the first attachment element and the second attachment element so that the first tube and the second tube extend in spaced relation to one another between the first attachment element and the second attachment element when the first attachment element and the second attachment element are spaced from one another, the first geometric configuration and the second geometric configuration being different from one another.

18. The tubing set defined in claim 17, wherein the first attachment element and the second attachment element include coupling elements for quick-release securing of the first attachment element and the second attachment element to the panel of the console at the first seat and the second seat.

19. The tubing set defined in claim 18, wherein the coupling elements include magnets.

20. The tubing set defined in claim 17, wherein the first attachment element and the second attachment element are disks of different sizes.

\* \* \* \* \*